US008725255B2

(12) United States Patent
Arcot-Krishnamurthy et al.

(10) Patent No.: US 8,725,255 B2
(45) Date of Patent: May 13, 2014

(54) CARDIAC RESYNCHRONIZATION THERAPY OPTIMIZATION USING CARDIAC ACTIVATION SEQUENCE INFORMATION

(75) Inventors: Shantha Arcot-Krishnamurthy, Roseville, MN (US); Yi Zhang, Blaine, MN (US); Jiang Ding, Maplewood, MN (US); Yinghong Yu, Shoreview, MN (US); Yanting Dong, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 723 days.

(21) Appl. No.: 11/601,216

(22) Filed: Nov. 17, 2006

(65) Prior Publication Data
US 2008/0119903 A1 May 22, 2008

(51) Int. Cl.
*A61N 1/365* (2006.01)
*A61N 1/362* (2006.01)

(52) U.S. Cl.
USPC ................................. 607/9; 607/17

(58) Field of Classification Search
USPC ............... 607/2, 4, 5, 7, 9, 10, 11, 17, 15, 27; 600/508–522
See application file for complete search history.

(56) References Cited

U.S. PATENT DOCUMENTS

| | | | |
|---|---|---|---|
| 4,136,690 A * | 1/1979 | Anderson et al. | 600/512 |
| 4,697,597 A * | 10/1987 | Sanz et al. | 600/512 |
| 5,417,717 A | 5/1995 | Salo et al. | |
| 5,803,084 A * | 9/1998 | Olson | 600/512 |
| 6,021,331 A | 2/2000 | Cooper et al. | |
| 6,021,351 A | 2/2000 | Kadhiresan et al. | |
| 6,044,298 A | 3/2000 | Salo et al. | |
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,285,906 B1 | 9/2001 | Ben-Haim et al. | |
| 6,312,378 B1 | 11/2001 | Bardy | |
| 6,336,903 B1 | 1/2002 | Bardy | |

(Continued)

FOREIGN PATENT DOCUMENTS

| | | |
|---|---|---|
| JP | 2005538776 | 12/2005 |
| WO | WO02094372 | 11/2002 |
| WO | WO 2006/039693 | 4/2006 |
| WO | WO2006039693 | 4/2006 |

OTHER PUBLICATIONS

U.S. Appl. No. 11/479,877, Jun. 30, 2006, Arcot-Krishnamurthy et al.

(Continued)

*Primary Examiner* — Allen Porter, Jr.
(74) *Attorney, Agent, or Firm* — Brooks, Cameron & Huebsch, PLLC

(57) ABSTRACT

Systems and methods provide for pacing a heart to improve pumping efficiency of the heart, such as by producing a cardiac fusion response for patient's subject to cardiac resynchronization therapy. A pacing parameter, such as an A-V delay, V-V delay, lead/electrode configuration or vector, is adjusted and a cardiac signal vector representative of all or a portion of one or more cardiac activation sequences is monitored during pacing parameter adjustment. A change in a characteristic of the cardiac signal vector is detected in response to an adjusted pacing parameter, the change indicative of a cardiac fusion response. A pacing therapy may be delivered to produce the cardiac fusion response using the adjusted pacing parameter.

21 Claims, 11 Drawing Sheets

(56) References Cited

U.S. PATENT DOCUMENTS

| | | | |
|---|---|---|---|
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 6,473,645 B1 | 10/2002 | Levine | |
| 6,522,915 B1* | 2/2003 | Ceballos et al. | 600/509 |
| 6,567,700 B1 | 5/2003 | Turcott et al. | |
| 6,606,516 B2 | 8/2003 | Levine | |
| 6,708,061 B2 | 3/2004 | Salo et al. | |
| 6,754,523 B2* | 6/2004 | Toole | 600/509 |
| 6,795,732 B2 | 9/2004 | Stadler et al. | |
| 6,832,112 B1* | 12/2004 | Bornzin | 607/9 |
| 6,876,881 B2 | 4/2005 | Baumann et al. | |
| 6,909,916 B2 | 6/2005 | Spinelli et al. | |
| 6,915,160 B2 | 7/2005 | Auricchio et al. | |
| 6,965,797 B2 | 11/2005 | Pastore et al. | |
| 6,973,349 B2 | 12/2005 | Salo | |
| 6,980,851 B2 | 12/2005 | Zhu et al. | |
| 6,999,815 B2 | 2/2006 | Ding et al. | |
| 7,010,347 B2 | 3/2006 | Schecter | |
| 7,013,176 B2 | 3/2006 | Ding et al. | |
| 7,041,061 B2 | 5/2006 | Kramer et al. | |
| 7,113,823 B2 | 9/2006 | Yonce et al. | |
| 7,177,688 B2 | 2/2007 | Salo et al. | |
| 7,181,284 B2 | 2/2007 | Burnes | |
| 7,209,786 B2 | 4/2007 | Brockway et al. | |
| 7,239,913 B2 | 7/2007 | Ding et al. | |
| 7,257,443 B2 | 8/2007 | Pastore et al. | |
| 7,292,887 B2 | 11/2007 | Salo et al. | |
| 7,310,554 B2 | 12/2007 | Kramer et al. | |
| 7,319,900 B2 | 1/2008 | Kim et al. | |
| 7,346,394 B2 | 3/2008 | Liu et al. | |
| 2001/0003159 A1* | 6/2001 | Dooley et al. | 607/9 |
| 2002/0007198 A1* | 1/2002 | Haupert et al. | 607/30 |
| 2003/0078624 A1* | 4/2003 | Carlson et al. | 607/9 |
| 2003/0078630 A1* | 4/2003 | Lovett et al. | 607/27 |
| 2004/0102812 A1 | 5/2004 | Yonce et al. | |
| 2005/0055058 A1 | 3/2005 | Mower | |
| 2005/0102002 A1 | 5/2005 | Salo et al. | |
| 2005/0131476 A1 | 6/2005 | Kim et al. | |
| 2005/0209648 A1* | 9/2005 | Burnes et al. | 607/9 |
| 2005/0216066 A1 | 9/2005 | Auricchio et al. | |
| 2006/0069322 A1 | 3/2006 | Zhang et al. | |
| 2006/0235478 A1* | 10/2006 | Van Gelder et al. | 607/9 |
| 2006/0247698 A1* | 11/2006 | Burnes et al. | 607/9 |
| 2008/0255629 A1 | 10/2008 | Jenson et al. | |

OTHER PUBLICATIONS

Restriction dated Jun. 26, 2008 from U.S. Appl. No. 11/279,877, 6 pages.
Restriction response submitted Aug. 8, 2008 from U.S. Appl. No. 11/279,877, 6 pages.
Office Action Response submitted Mar. 6, 2009 to office action dated Oct. 8, 2008 from U.S. Appl. No. 11/479,877, 9 pages.
Office Action Response submitted Aug. 24, 2009 to office action dated Jul. 2, 2009 from U.S. Appl. No. 11/479,877, 10 pages.
Office Action Response submitted Feb. 24, 2010 to office action dated Dec. 9, 2009 from U.S. Appl. No. 11/479,877, 8 pages.
Office Action dated Jun. 11, 2010 from U.S. Appl. No. 11/479,877, 8 pages.
Office Action Response dated Sep. 22, 2009 from U.S. Appl. No. 11/479,877, 10 pages.
Office Action dated Aug. 27, 2009 from U.S. Appl. No. 11/479,877, 3 pages.
Interview Summary dated Mar. 6, 2009 from U.S. Appl. No. 11/479,877, 2 pages.
Office Action Response dated Mar. 17, 2009 from European Application No. 07796501.0, 14 pages.
Office Action dated Oct. 30, 2009 from European Application No. 07796501.0, 4 pages.
Office Action Response dated Apr. 28, 2010 from European Application No. 07796501.0, 9 pages.
Office Action Response dated Oct. 23, 2009 from European Application No. 07867460.3, 7 pages.
Office Action dated Jun. 7, 2010 from European Application No. 07796501.0, 4 pages.
International Preliminary Report on Patentability dated Jan. 15, 2009 from PCT Application No. PCT/US2007/014934, 9 pages.
International Search Report and Written Opinion dated Nov. 23, 2007 from PCT Application No. PCT/US2007/014934, 15 pages.
International Preliminary Report on Patentability dated May 28, 2009 from PCT Application No. PCT/US2007/023988, 5 pages.
International Search Report and Written Opinion dated May 20, 2008 from PCT Application No. PCT/US2007/023988, 13 pages.
Office Action from U.S. Appl. No. 11/479,877 dated Dec. 9, 2009, 11 pages.
Office Action from U.S. Appl. No. 11/479,877 dated Jul. 2, 2009, 10 pages.
Office Action from U.S. Appl. No. 11/479,877 dated Oct. 8, 2008, 12 pages.
File History for U.S. Appl. No. 11/479,877 as retrieved from U.S. Patent and Trademark Office Pair System on Jan. 17, 2011, 303 pagesp.
File History for EP Application No. 07867460.3 as retrieved from European Patent Office System on Jan. 17, 2011, 170 pages.
File History for EP Application No. 07796501.0 as retrieved from European Patent Office System on May 31, 2012, 285 pages.
File History for U.S. Appl. No. 11/479,877, May 31, 2012.
File History for EP Application No. 07867460.3 as retrieved from European Patent Office System on Nov. 1, 2011, 79 pages.
File History for EP Application No. 07796501.0 as retrieved from European Patent Office System on Nov. 1, 2011, 170 pages.
File History for U.S. Appl. No. 11/479,877, Nov. 29, 2011.
File History for EP Application No. 07867460.3 as retrieved from European Patent Office System on Jul. 25, 2012, 176 pages.

* cited by examiner

CARDIAC RESYNCHRONIZATION THERAPY OPTIMIZATION USING CARDIAC ACTIVATION SEQUENCE INFORMATION

FIELD OF THE INVENTION

The present invention relates generally to medical devices that deliver cardiac electrical therapy and, more particularly, to cardiac stimulation devices that optimize cardiac resynchronization therapy using cardiac activation sequence information.

BACKGROUND OF THE INVENTION

Rhythmic contractions of a healthy heart are normally controlled by the sinoatrial (SA) node which includes specialized cells located in the superior right atrium. The SA node is the normal pacemaker of the heart, typically initiating 60-100 heart beats per minute. When the SA node is pacing the heart normally, the heart is said to be in normal sinus rhythm.

The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways can suffer compromised cardiac output. Cardiac rhythm management devices have been developed that provide pacing stimulation to one or more heart chambers in an attempt to improve the rhythm and coordination of atrial and/or ventricular contractions.

SUMMARY OF THE INVENTION

The present invention is directed to systems and methods for pacing a heart to improve pumping efficiency of the heart. Embodiments of the present invention are directed to pacing therapies that produce a cardiac fusion response for patient's subject to cardiac resynchronization therapy. Embodiments of the present invention are also directed to optimizing therapy parameters and modifying therapy delivery based on one or more characteristics of a patient's cardiac activation sequence.

According to embodiments of the present invention, methods for producing a cardiac fusion response involve obtaining a cardiac signal vector associated with all or a portion of one or more cardiac activation sequences. A pacing parameter, such as an A-V delay, V-V delay, lead/electrode configuration or vector, is adjusted and the cardiac signal vector is monitored during pacing parameter adjustment. A change in a characteristic of the cardiac signal vector is detected in response to an adjusted pacing parameter, the change indicative of a cardiac fusion response. A pacing therapy is delivered to produce a cardiac fusion response using the adjusted pacing parameter.

Detecting the change in the cardiac signal vector characteristic may involve detecting a change in an angle or a magnitude (or both) of the cardiac signal vector. The change in the cardiac signal vector characteristic indicative of the cardiac fusion response may be detected for a range of pacing parameters or parameter values, and the pacing therapy may be delivered using the adjusted pacing parameter falling within the range of pacing parameters or parameter values. Detecting the change in cardiac signal vector characteristic may involve detecting a change between intrinsic cardiac activation and therapy-initiated cardiac activation.

According to one approach, a change in a cardiac signal vector indicative of intrinsic cardiac activation is detected relative to a baseline. In response to this change in intrinsic cardiac activation, pacing parameter adjustment and detection of a change in the cardiac signal vector characteristic indicative of a fusion response are repeated. The adjusted or updated pacing parameter that produces a fusion response is stored for subsequent pacing therapy delivery. This update process may be initiated automatically or in response to local or remote user input.

Methods of the present invention may involve detecting a change in a cardiac signal vector indicative of therapy-initiated cardiac activation relative to a first baseline and absence of change in a cardiac signal vector indicative of intrinsic cardiac activation relative to a second baseline. In response to the detected change, the pacing parameter is adjusted to produce the cardiac fusion response for subsequent pacing therapy delivery. Methods may involve accessing a look-up table of pacing parameters pre-established for the patient, such that the pacing parameters of the look-up table, when implemented, produce a cardiac fusion response for the patient. The adjusted pacing parameter may be selected from the look-up table.

According to other embodiments of the present invention, systems may be implemented to include a plurality of electrodes configured for sensing cardiac electrical activity and energy delivery. A signal processor is coupled to the electrodes and configured to produce a cardiac signal vector associated with all or a portion of one or more cardiac activation sequences. A controller is coupled to the electrodes and the signal processor.

The controller is configured to adjust a pacing parameter and detect a change in a characteristic of the cardiac signal vector in response to an adjusted pacing parameter, the change indicative of a cardiac fusion response. The controller may be further configured to deliver a pacing therapy to produce the cardiac fusion response using the adjusted pacing parameter. The change in characteristic of the cardiac signal vector detected by the controller may indicate a change between pacing-dominant cardiac activation, fusion, and intrinsic-dominant cardiac activation.

The controller may be disposed within an implantable housing, a patient-external housing, or distributed in both the implantable and patient-external housing. The signal processor may be disposed within an implantable housing, a patient-external housing, or distributed in both the implantable and patient-external housing. The plurality of electrodes may comprise implantable electrodes, cutaneous electrodes, or a combination of implantable and cutaneous electrodes.

In some configurations, the controller and the signal processor may be provided in an implantable housing, and the electrodes may comprise implantable electrodes coupled to, or provided on, the housing. In other configuration, the controller and the signal processor may be provided in a patient-external housing, and the electrodes preferably comprise cutaneous electrodes coupled to the housing.

The controller may be coupled to memory configured to store a look-up table comprising pacing parameters associated with one or both of heart rate and patient condition, the pacing parameters established to produce a cardiac fusion response. The pacing parameters stored in the look-up table may include A-V and V-V delay parameters, electrode/lead configurations, pacing vectors, and other parameters that influence cardiac pacing. The controller may be configured to update the look-up table with updated pacing parameters in response to a change in the cardiac signal vector characteristic indicative of pace-dominant or intrinsic-dominant cardiac activation, the updated pacing parameters established to produce a cardiac fusion response for the patient. The controller may, in response to a change in the cardiac signal vector characteristic indicative of a change in intrinsic-dominant cardiac activation, be configured to update the look-up table with updated baseline values characterizing each of the patient's intrinsic-dominant cardiac activation and pace-dominant cardiac activation.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
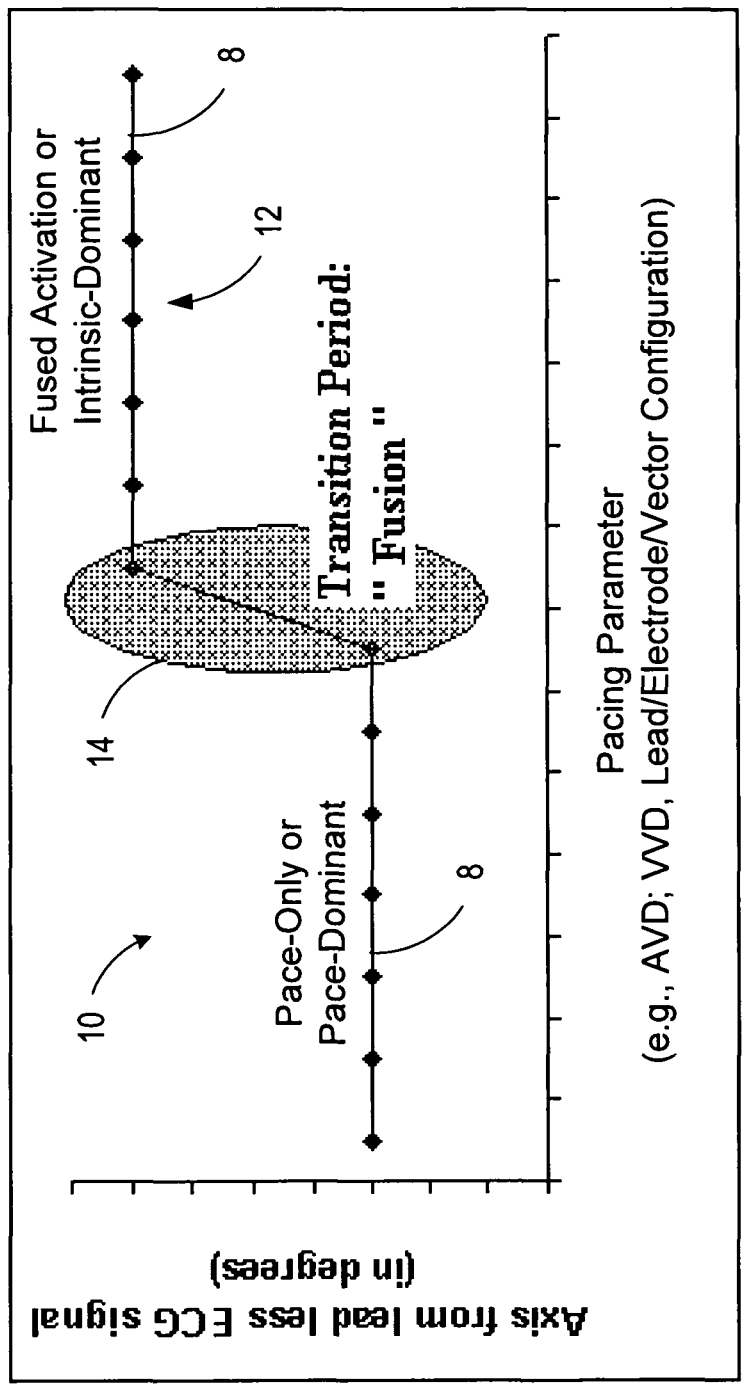
FIG. 1 is a diagram that illustrates the influence that a pacing parameter has on the patient's cardiac activation sequence in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A medical device implemented according to the present invention may include one or more of the features, structures, methods, or combinations thereof described hereinbelow. For example, a cardiac stimulator may be implemented to include one or more of the advantageous features and/or processes described herein. It is intended that such a stimulator or other implanted or patient-external device need not include all of the features described herein, but may be implemented to include selected features that provide for useful structures and/or functionality. Such a device may be implemented to provide a variety of therapeutic or diagnostic functions.

A wide variety of cardiac stimulation devices may be configured to implement a cardiac therapy methodology of the present invention. A non-limiting representative list of such devices includes pacemakers, cardiovertors, defibrillators, resynchronizers, and other cardiac monitoring and therapy delivery devices. These devices may be configured with a variety of electrode arrangements, including cutaneous, transvenous, endocardial, and epicardial electrodes (i.e., intrathoracic electrodes), and/or subcutaneous, non-intrathoracic electrodes, such as can, header and/or indifferent electrodes, subcutaneous array electrodes and/or lead electrodes (i.e., non-intrathoracic electrodes).

Embodiments of the present invention are directed to monitoring and updating characteristics of a patient's cardiac activation sequence during intrinsic cardiac activation ($CA_{INT}$) and therapy-initiated cardiac activation ($CA_{TX}$). The degree of changes in $CA_{INT}$ or $CA_{TX}$ is used to recommend the need for adjustment or re-optimization of therapy parameters. Therapy parameters, such as A-V delay, V-V delay, pacing site, and pacing configuration, can be changed and changes in the patient's cardiac activation sequence monitored. These changes may be used to identify a patient's cardiac fusion response and to recommend parameters that can produce a fusion response. Selection of these therapy parameters can be effected automatically by the therapy delivery device or through user input, such as by use of a local programmer or personal communicator, or remotely via a networked server system, such as a server-based advanced patient management (APM) system. An example of a user is a clinician.

To improve pumping efficiency in patients subject to cardiac resynchronization therapy (CRT), it is desirable to achieve a certain level of fusion, whereby a pacing pulse effectively merges with an intrinsic response of a heart chamber. Selection of proper therapy parameters of the therapy delivery device that delivers the pacing pulse is critical in order to achieve fusion. Reliable detection of a cardiac fusion response is necessary in order to determine the proper therapy parameters that will produce the desired cardiac fusion response.

Embodiments of the present invention are directed to improving pumping efficiency in CRT patients by selection of appropriate therapy parameters based on one or more characteristics of the patient's cardiac activation sequence. Embodiments of the present invention are also directed to detection of a cardiac fusion response and storing of therapy parameters that can be used by a therapy delivery device to produce a fusion response during therapy delivery.

Embodiments of the present invention are further directed to determining changes in cardiac activation sequence characteristics associated with intrinsic and therapy-based cardiac activation. Deviations in intrinsic cardiac activation from an established baseline may be indicative of a change in cardiac condition, such as a change resulting from ischemia, myocardial infarction or remodeling, for example. Detection of such deviations may be used to trigger an alert regarding the cardiac condition change and/or a request to a user that re-optimization of therapy parameters is needed. Detection of such deviations may trigger an automatic re-optimization of therapy parameters.

Deviations in therapy-based cardiac activation from an established baseline, in the absence of a deviation in intrinsic cardiac activation, are indicative of change in patient condition, such as activity level (e.g., exercise) or posture, for example. Changes in therapy-based cardiac activation may be used to trigger a change in pacing parameters to improve cardiac pumping efficiency in response to changes in such patient dynamics. In response to changed therapy-based cardiac activation characteristics, new therapy parameters may be obtained, such as from a look-up table, and implemented by the therapy delivery device. If new therapy parameters are not available (e.g., not included in the look-up table), a re-optimization procedure may be performed to obtain therapy parameters appropriate for the change in patient dynamics.

Re-optimization of therapy parameters typically involves the determination of updated (or new) therapy parameters that will improve pumping efficiency in the patient in view of the change in cardiac condition and/or patient dynamics. The updated or new therapy parameters are preferably stored in a look-up table or other data structure for access by the therapy delivery device. If a change in intrinsic cardiac activation is detected, then it is assumed that a pathological change has occurred in the patient's cardiac condition. In this case, a re-optimization procedure is preferably performed to obtain new baselines for both intrinsic and therapy-based cardiac activation. Updated therapy parameters may then be determined that will improve a patient's pumping efficiency, such as by implementing a cardiac resynchronization therapy using therapy parameters that will produce a cardiac fusion response.

Re-optimization may also involve implementing a pacing site selection procedure, whereby one or more electrodes, temporal sequence, and/or pulse waveform characteristics are selected or modified for delivery of pacing to enhance the contractile function of a heart chamber. Pacing site optimization may be implemented in accordance with methodologies disclosed in commonly owned U.S. Publication No. 2008/0004667, which is hereby incorporated herein by reference.

According to embodiments of the present invention, characteristics of all or a portion of one or more cardiac activation sequences are obtained. The characteristics may include timing (durations) and morphology (e.g., extracted morphological features) of P, QRS, T, and/or U waves of the patient's cardiac activation sequence. For example, characteristics such as amplitude (magnitude) and direction of a cardiac signal vector indicative of all or a portion of one or more cardiac activation sequences are obtained. These characteristics are obtained during intrinsic cardiac activation ($CA_{INT}$), such as during rest, and during therapy-initiated cardiac activation ($CA_{TX}$), such as during delivery of a pacing therapy using therapy parameters optimized in accordance with embodiments of the present invention.

Baselines for intrinsic and therapy-initiated cardiac activation characteristics are established, such as by trending these characteristics over time. Deviations of the intrinsic and therapy-initiated cardiac activation characteristics from their respective baselines are detected, and the need for re-optimizing therapy parameters is identified. As therapy parameter(s) are systematically changed, the influence of these changed parameter(s) on the patient's cardiac activation sequence is detected or estimated in order to select therapy parameter(s) that can improve a patient's pumping efficiency, such as by selection of therapy parameters that will produce a cardiac fusion response. Therapy parameters may be optimized (i.e., determined or adjusted so that improved pumping efficiency is achieved) by tracking the influence that therapy parameter(s) have on the patient's cardiac activation sequence.

Turning now to FIG. 1, there is shown a diagram that illustrates the influence that a pacing parameter has on the patient's cardiac activation sequence. FIG. 1 illustrates the change in the angle of a cardiac signal vector 8 as a function of pacing parameter change, where the cardiac signal vector can represent all or a portion of one or more cardiac activation sequences. The pacing parameter may be an A-V delay, a V-V delay parameter, a lead/electrode configuration or a pacing vector, for example.

The cardiac signal vector in region 10 of FIG. 1 indicates pace-only or pace-dominant cardiac activation. The cardiac signal vector in region 12 indicates fused activation or intrinsic-dominant cardiac activation. Until fusion is reached, the pacing activation (region 10) dominates the cardiac activation sequence. In the vicinity of fusion, shown in region 14, there is a significant contribution from intrinsic conduction, which results in a significant change in the magnitude and/or direction of the cardiac signal vector. FIG. 1 shows this change in terms of a change in axis angle of the cardiac signal vector 8. The amount of change in a characteristic of the cardiac signal vector is patient-dependent. Therefore, a patient-specific threshold for detecting fusion using a deviation in one or more characteristics of the patient's cardiac signal vector may be determined at implant and later updated, such as during regular follow-up visits with a clinician.

As is shown in FIG. 1, the patient's cardiac fusion response is associated with a transition region or period 14 between pace-only/pace-dominant and fused activation/intrinsic-dominant cardiac activation. This fusion region 14 is associated with a range or set of pacing parameters that can produce fusion (e.g., a range of A-V and/or V-V delay parameters, a set of lead/electrode configurations, or set of pacing vectors). Pacing parameter selection may be made to produce "desirable" or a pre-selected degree of fusion. The degree of fusion may be dependent on the degree of patient-dyssynchrony. For example, patients with wide QRS complexes may exhibit a higher degree of fusion, whereas patients with narrower QRS complexes may show a lesser degree of fusion. Once the patient's cardiac fusion response is identified, the pacing parameters that produced the desired fusion response may be stored and used during pacing therapy.

Figure 2:
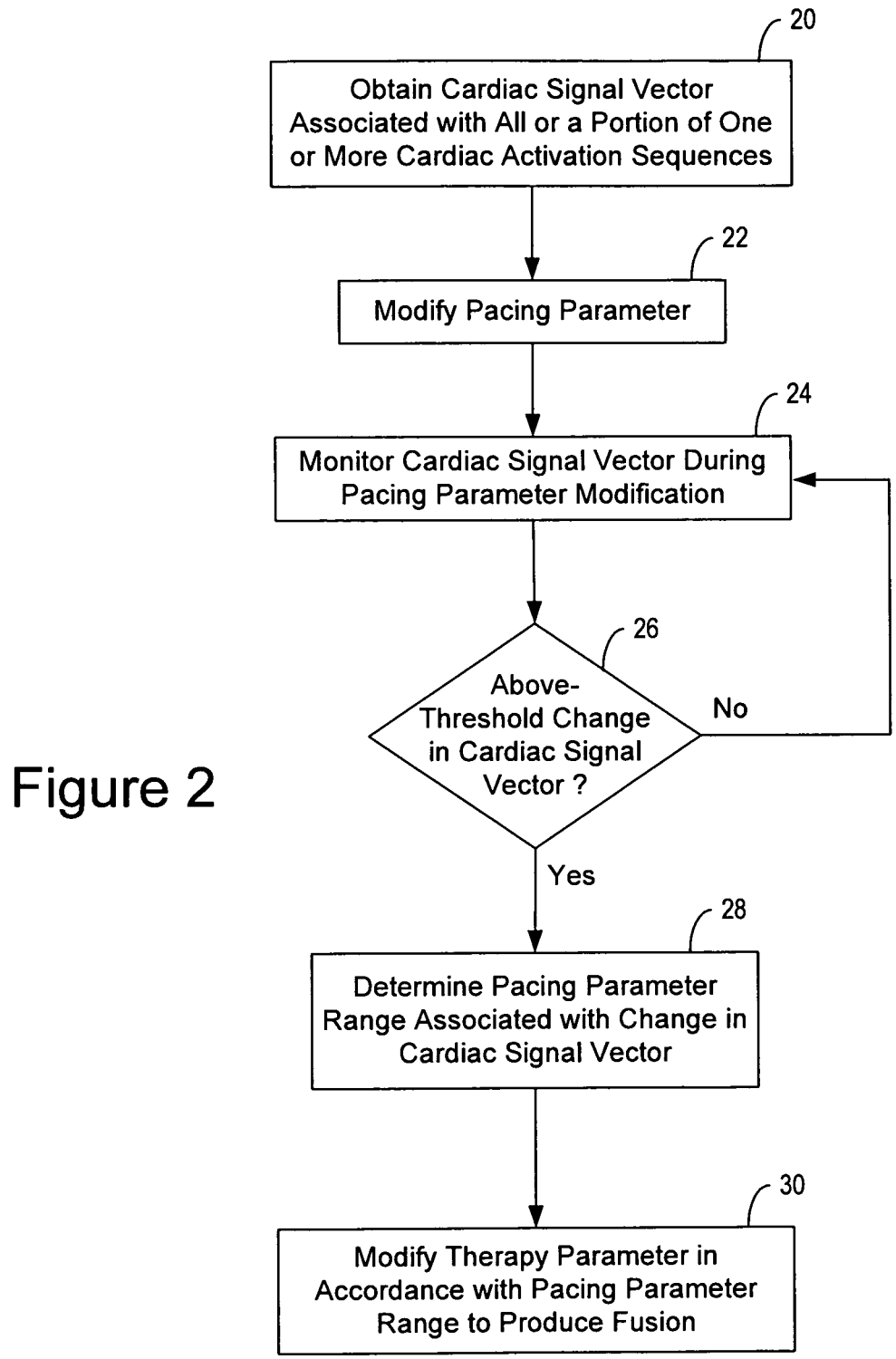
FIG. 2 is a diagram of various processes associated with pacing parameter optimization in accordance with an embodiment of the present invention.

FIG. 2 is a diagram of various processes associated with pacing parameter optimization in accordance with an embodiment of the present invention. According to FIG. 2, a cardiac signal vector associated with all or a portion of one or more cardiac activation sequences is obtained 20. A pacing parameter, such as A-V or V-V delay, lead/electrode configuration or vector, is adjusted 22, and the cardiac signal vector monitored 24 during pacing parameter adjustment. It is understood that more than one pacing parameter may be adjusted at the same time and the results of such adjustments monitored. Pacing parameter adjustment and monitoring of the cardiac signal vector continue until a change in the cardiac signal vector is detected. If a change in a characteristic (e.g., magnitude or angle) of the cardiac signal vector above a threshold (e.g., patient-dependent threshold) is detected 26, such as that indicative of a change from pace-dominant to intrinsic-dominant cardiac activation (or vice-versa), the pacing parameter or pacing parameter range associated with the change (e.g., fusion transition region) is determined 28. A pacing therapy may be modified 30 by using this pacing parameter(s) to produce a cardiac fusion response.

Figure 3:
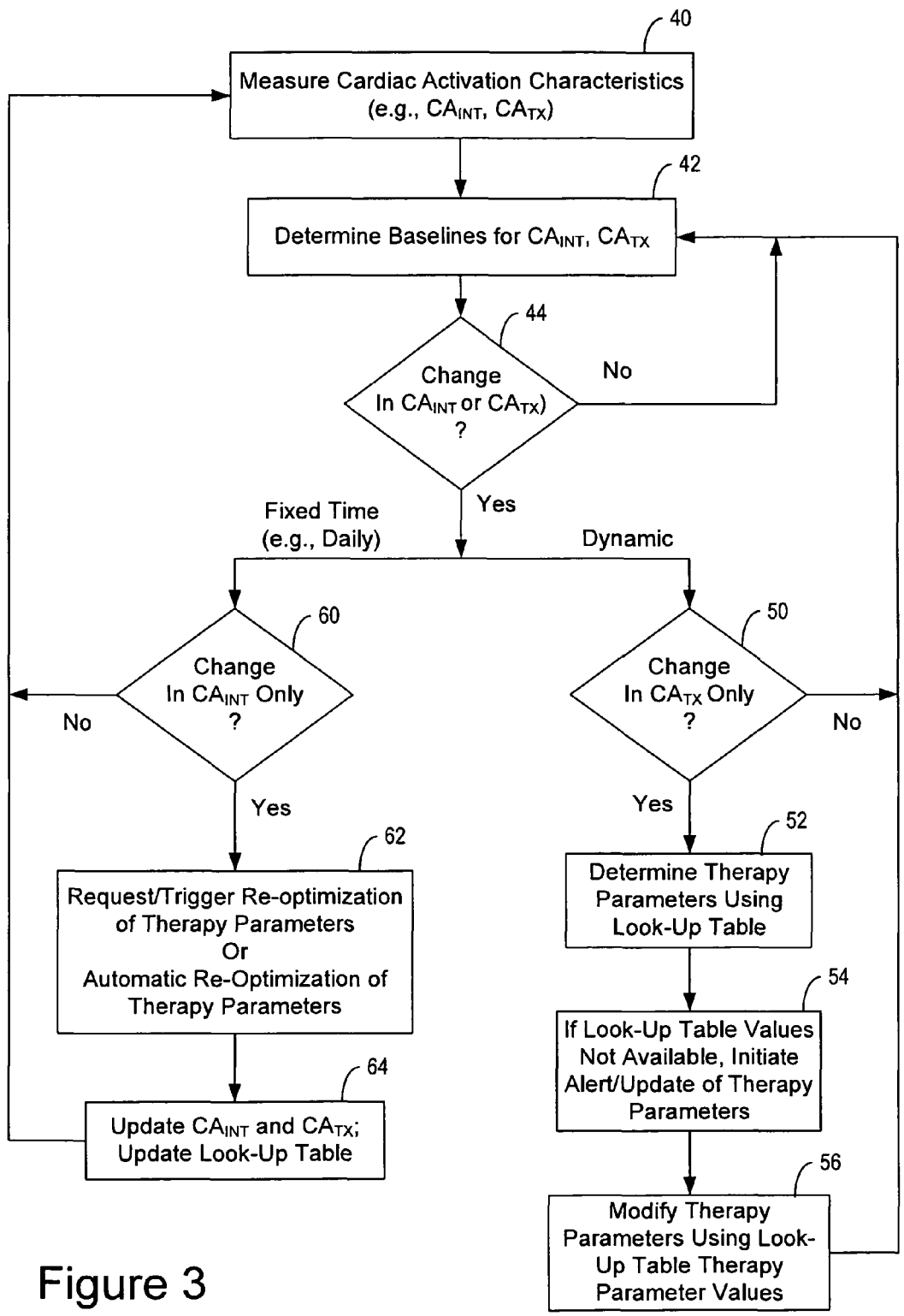
FIG. 3 is a diagram of various processes associated with pacing parameter optimization in accordance with another embodiment of the present invention.

FIG. 3 is a diagram of various processes associated with pacing parameter optimization in accordance with another embodiment of the present invention. According to FIG. 3, one or more cardiac activation sequence characteristics are measured 40 for intrinsic ($CA_{INT}$) and therapy-based ($CA_{TX}$) cardiac activation. Baselines for both intrinsic and therapy-based cardiac activation are established, such as by averaging $CA_{INT}$ and $CA_{TX}$ characteristic values over time.

If no significant change in $CA_{INT}$ or $CA_{TX}$ characteristic values is detected, as is tested at decision block 44, the baseline determination processes 42 continue. A significant change in a $CA_{INT}$ or $CA_{TX}$ characteristic values may be determined based on a patient-specific threshold, as discussed previously, or a statistically significant deviation (e.g., ≥3 sigma from standard deviation; ≥x % change) relative to baseline. If a significant change in $CA_{INT}$ or $CA_{TX}$ characteristic values is detected, then a check is made to determine if the change is a result of a change in the patient's cardiac condition or activity level/posture.

If a change in a $CA_{TX}$ characteristic value is detected 50 with no appreciable change in a $CA_{INT}$ characteristic value, then it is assumed that a change in patient dynamics has been detected. In order to improve cardiac pumping efficiency in view of the change in patient dynamics, one or more therapy parameters may be adjusted to accommodate such chance. According to one approach, a look-up table of therapy parameters pre-established for the patient may be accessed 52. The look-up table preferably includes a matrix of heart/pacing rates and associated pacing parameters (A-V and/or V-V delays, lead/electrode configurations, pacing vectors) that were determined to produce a cardiac fusion response for the patient, such as by using the methodology illustrated in FIG. 2. For example, the look-up table may include electrode location and pacing vector information for one or more leads, such as a multi-polar lead, active can electrodes, indifferent electrodes, and subcutaneous electrode arrays, among others.

The look-up table may include other parameters, such as posture positions/angles and activity levels, for example. Based on changes in patient dynamics (e.g., heart rate, posture, activity level), appropriate therapy parameters may be obtained from the look-up table. Therapy parameter(s) used by the therapy delivery device may be modified 56 to include the parameter(s) obtained from the look-up table, and therapy may be delivered to the patient based on the modified therapy parameter(s).

If a therapy parameter is not available in the look-up table for a given patient dynamic condition, a re-optimization procedure may be performed to determine such unavailable parameter. The methodology illustrated in FIG. 2 may be implemented to determine 54 the previously unavailable parameter. For example, the clinician may systematically have the patient exercise and/or orient the patient in various positions while one or more pacing parameters are adjusted to produce a fusion response. Patient dynamic condition parameters and associated therapy parameters may be stored as new or updated data entries in the look-up table.

An alert may be initiated 54 for clinician recognition that look-up table updating is needed, such as by way of a programmer or APM alert. A request for look-up table updating may also be generated and communicated to the clinician via a programmer or APM message. A look-up table update procedure may be initiated automatically by the therapy delivery device or in response to clinician input/instruction.

If a change in a $CA_{INT}$ characteristic value is detected, as is tested at decision block 60, then it is assumed that a pathological change has occurred in the patient's cardiac condition. A request for, or triggering of, a re-optimization procedure may be initiated 62. In response to the trigger or clinician input/instruction, a re-optimization procedure is performed 62 to obtain new baseline characteristics for both intrinsic ($CA_{INT}$) and therapy-based ($CA_{TX}$) cardiac activation. Updated therapy parameters are also determined 62, as in a manner discussed above, in view of the pathological change in the patient's cardiac condition. The updated therapy parameters and baseline characteristics for $CA_{INT}$ and $CA_{TX}$ are stored 64 in the look-up table. The processes depicted in FIG. 3 are then repeated based on the look-up table updates.

Cardiac activation sequence monitoring and/or tracking according to the present invention preferably employs more than two electrodes of varying location, and possibly of varying configuration. As discussed previously, the electrodes may be cutaneous, subcutaneous or intrathoracic electrodes, or any combination of such electrodes.

Electrocardiogram (ECG) signals originate from electrophysiological signals propagated through the heart muscle, which provide for the cardiac muscle contraction that pumps blood through the body. A sensed ECG signal is effectively a superposition of all the depolarizations occurring within the heart that are associated with cardiac contraction, along with noise components. The propagation of the depolarizations through the heart may be referred to as a depolarization wavefront. The sequence of depolarization wavefront propagation through the chambers of the heart, providing the sequential timing of the heart's pumping, is designated a cardiac activation sequence.

Various known approaches may be used to separate activation sequence components of ECG signals, and produce one or more cardiac signal vectors associated with all or a portion of one or more cardiac activation sequences based on the separation. The activation sequence components may be considered as the signal sources that make up the ECG signals, and the signal separation process may be referred to as a source separation process or simply source separation. One illustrative signal source separation methodology useful for producing cardiac signal vectors associated with cardiac activation sequences is designated blind source separation, and is described in greater detail in commonly owned U.S. Pat. No. 7,890,159, which is hereby incorporated herein by reference.

In general, the quality of the electrocardiogram or electrogram sensed from one pair of electrodes of a cardiac therapy device depends on the orientation of the electrodes with respect to the depolarization wavefront produced by the heart. The signal sensed on an electrode bi-pole is the projection of the ECG vector in the direction of the bi-pole. Cardiac activation sequence monitoring and/or tracking algorithms advantageously exploit the strong correlation of signals from a common origin (the heart) across spatially distributed electrodes.

Figure 4A:
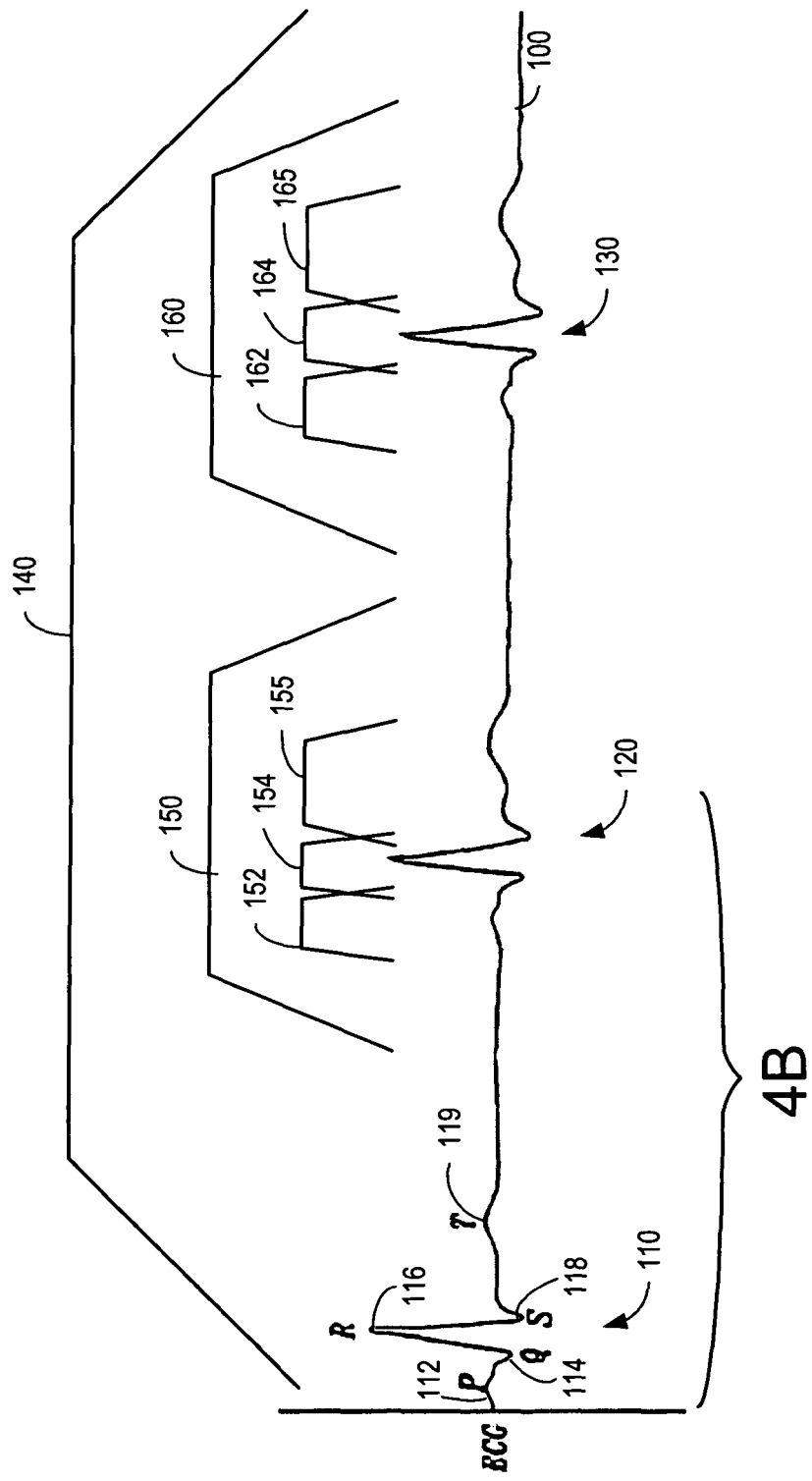
FIGS. 4A and 4B are pictorial diagrams of an electrocardiogram (ECG) waveform for three consecutive heartbeats (FIG. 4A) and a magnified portion of the electrocardiogram (ECG) waveform for the first two consecutive heartbeats (FIG. 4B)
Figure 4B:
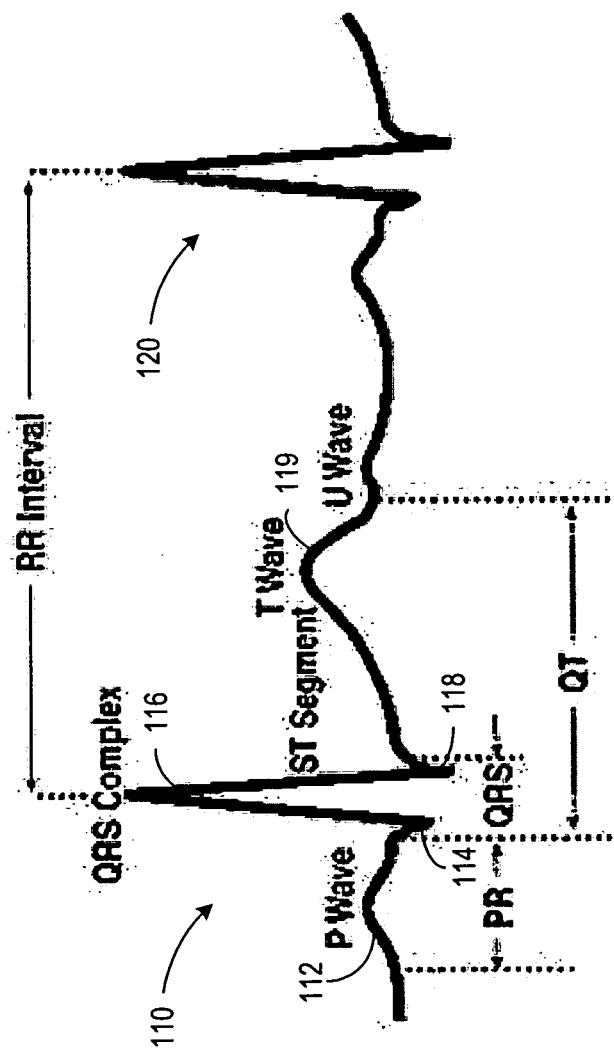

Referring to FIGS. 4A and 4B, an ECG waveform 100 describes the activation sequence of a patient's heart as recorded, for example, by a bi-polar cardiac sensing electrode. The graph of FIG. 4A illustrates an example of the ECG waveform 100 for three heartbeats, denoted as a first heartbeat 110, a second heartbeat 120, and a third heartbeat 130. FIG. 4B is a magnified view of the first two heartbeats 110, 120 of the ECG waveform identified by bracket 4B in FIG. 4A.

Referring to the first heartbeat 110, the portion of the ECG waveform representing depolarization of the atrial muscle fibers is referred to as a P-wave 112. Depolarization of the ventricular muscle fibers is collectively represented by a Q 114, R 116, and S 118 waves of the ECG waveform 100, typically referred to as the QRS complex, which is a well-known morphological feature of electrocardiograms. Finally, the portion of the waveform representing repolarization of the ventricular muscle fibers is known as a T-wave 119. Between contractions, the ECG waveform returns to an isopotential level.

The sensed ECG waveform 100 illustrated in FIGS. 4A and 4B is typical of a far-field ECG signal, effectively a superposition of all the depolarizations occurring within the heart that result in contraction. The ECG waveform 100 may also be obtained indirectly, such as by using a signal separation methodology.

Figure 5:
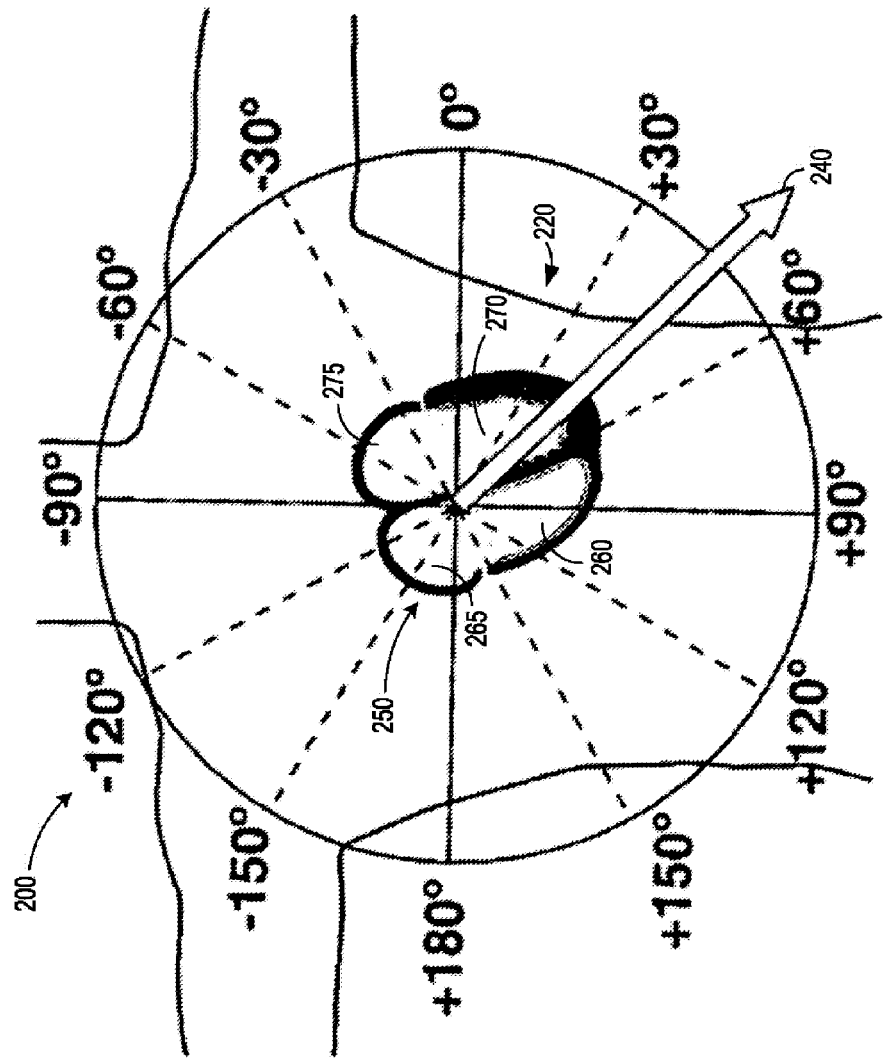
FIG. 5 is a polar plot of a cardiac signal vector superimposed over a frontal view of a thorax, with the origin of the polar plot located at the AV node of a patient's heart.

FIG. 5 illustrates a convenient reference for describing cardiac signal vectors associated with a depolarization wavefront. FIG. 5 is a polar plot 200 of a cardiac vector 240 superimposed over a frontal view of a thorax 220, with the origin of the polar plot located at a patient's heart 250, specifically, the atrioventricular (AV) node of the heart 250. The heart 250 is a four-chambered pump that is largely composed of a special type of striated muscle, called myocardium. Two major pumps operate in the heart, and they are a right ventricle 260, which pumps blood into pulmonary circulation, and a left ventricle 270, which pumps blood into systemic circulation. Each of these pumps is connected to its associated atrium, called a right atrium 265 and a left atrium 275.

The cardiac vector 240 is describable as having an angle, in degrees, about a circle of the polar plot 200, and having a magnitude, illustrated as a distance from the origin of the tip of the cardiac vector 240. The polar plot 200 is divided into halves by a horizontal line indicating 0 degrees on the patient's left, and +/−180 degrees on the patient's right, and further divided into quadrants by a vertical line indicated by −90 degrees at the patient's head and +90 degrees on the bottom. The cardiac vector 240 is projectable onto the two-dimensional plane designated by the polar plot 200.

The cardiac vector 240 is a measure of all or a portion of the projection of a heart's activation sequence onto the polar plot 200. The heart possesses a specialized conduction system that ensures, under normal conditions, that the overall timing of ventricular and atrial pumping is optimal for producing cardiac output, the amount of blood pumped by the heart per minute. The normal pacemaker of the heart is a self-firing unit located in the right atrium called the sinoatrial node. The electrical depolarization generated by this structure activates contraction of the two atria. The depolarization wavefront then reaches the specialized conduction system using conducting pathways within and between the atria. The depolarization is conducted to the atrioventricular node, and transmitted down a rapid conduction system composed of the right and left bundle branches, to stimulate contraction of the two ventricles.

Figure 6A:
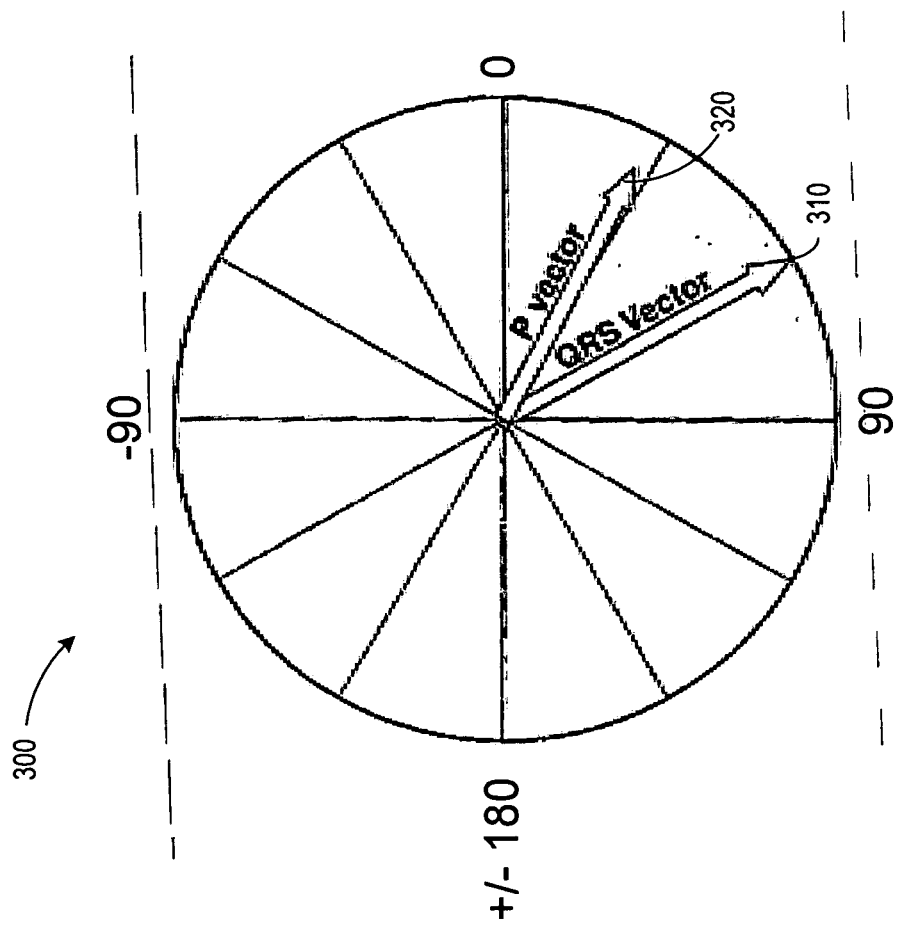
FIG. 6A is a polar plot of cardiac signal vectors showing QRS and P vectors in accordance with the present invention.

The cardiac vector 240 may be, for example, associated with the entire cardiac cycle, and describe the mean magnitude and mean angle of the cardiac cycle. Referring now to FIG. 6A, a polar plot 300 is illustrated of separate portions of the cardiac cycle that may make up the cardiac vector 240 of FIG. 5. As is illustrated in FIG. 6A, a QRS vector 310 and a P vector 320 are illustrated having approximately 60 degree and 30 degree angles, respectively. The QRS vector 310 may also be referred to as the QRS axis, and changes in the direction of the QRS vector may be referred to as QRS axis deviations.

The QRS vector 310 represents the projection of the mean magnitude and angle of the depolarization wavefront during the QRS portion of the cardiac cycle onto the polar plot 300. The P vector 320 represents the projection of the mean magnitude and angle of the depolarization wavefront during the P portion of the cardiac cycle onto the polar plot 300. The projection of any portion of the depolarization wavefront (e.g., P, QRS, T, U) may be represented as a vector on the polar plot 300.

Further, any number of cardiac cycles may be combined to provide a statistical sample that may be represented by a vector as a projection onto the polar plot 300. Likewise, portions of the cardiac cycle over multiple cardiac cycles may also be combined, such as combining a weighted summation of only the P portion of the cardiac cycle over multiple cardiac cycles, for example.

Referring now to FIGS. 4A through 6A, the first, second, and third cardiac cycles 110, 120, and 130 may be analyzed using a window 140 (FIG. 4A) applied concurrently to signals sensed by three or more cardiac sense electrodes. The ECG waveform signals 100 from all the sense electrodes, during the window 140, may be provided to a signal processor. The signal processor may then perform a source separation or other operation that provides the cardiac vector 240 (FIG. 5). The cardiac vector 240 then represents the orientation and magnitude of the cardiac vector that is effectively an average over all three cardiac cycles 110, 120, and 130.

Other windows are also useful. For example, a window 150 and a window 160 may provide each full cardiac cycle, such as the cardiac cycle 120 and the cardiac cycle 130 illustrated in FIG. 4A, to a controller for analysis. The windows 150, 160 may be useful for beat-to-beat analysis, where the angle, magnitude, or other useful parameter from the separated cardiac vector 240 is compared between consecutive beats, or trended, for example.

Examples of other useful windows include a P-window 152, a QRS window 154, and an ST window 155 (FIG. 4A) that provide within-beat vector analysis capability, such as by providing the P-vector 320 and the QRS-vector 310 illustrated in FIG. 6A. Providing a P-window 162 and/or a QRS-window 164, and/or an ST window 165 to subsequent beats, such as to the consecutive cardiac cycle 130 illustrated in FIG. 4A, provides for subsequent separations that may provide information for tracking and monitoring changes and/or trends of windowed portions of the cardiac cycle or statistical samples of P, QRS, or T waves over more than 1 beat.

Figure 6B:
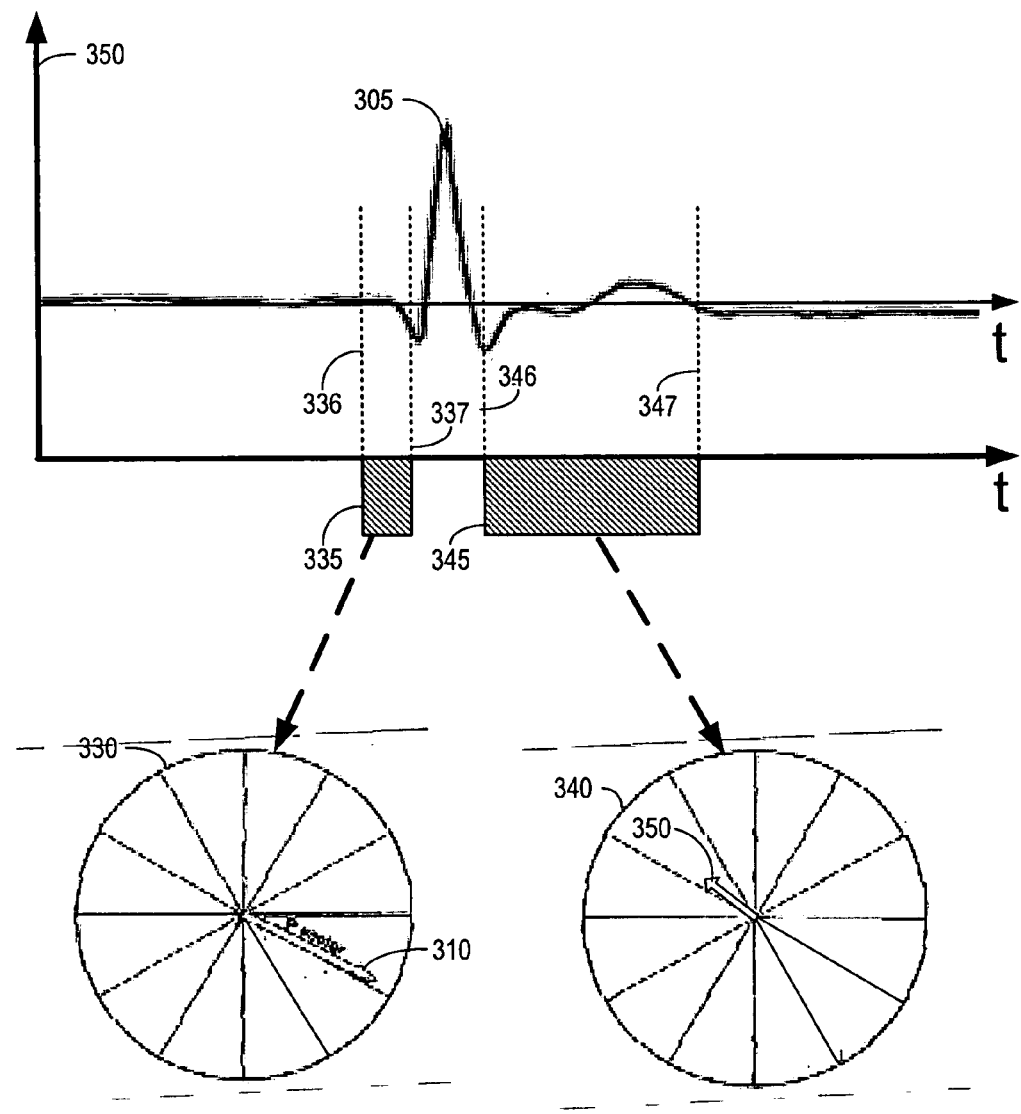
FIG. 6B illustrates polar plots of cardiac signal vectors obtained from selected portions of an electrocardiogram in accordance with the present invention.

Referring now to FIG. 6B, polar plots of cardiac vectors obtained from selected portions of an electrocardiogram are illustrated. In general, it may be desirable to define one or more detection windows associated with particular segments of a given patient's cardiac cycle. The detection windows may be associated with cardiac signal features, such as P, QRS, ST, and T wave features, for example. The detection windows may also be associated with other portions of the cardiac cycle that change in character as a result of changes in the pathology of a patient's heart. Such detection windows may be defined as fixed or triggerable windows.

Detection windows may include unit step functions to initiate and terminate the window, or may be tapered or otherwise initiate and terminate using smoothing functions such as Bartlett, Bessel, Butterworth, Hanning, Hamming, Chebyshev, Welch, or other functions and/or filters. The detection windows associated with particular cardiac signal features or segments may have widths sufficient to sense cardiac vectors resulting from normal or expected cardiac activity. Aberrant or unexpected cardiac activity may result in the failure of a given cardiac vector to fall within a range indicative of normal cardiac behavior. Detection of a given cardiac vector beyond a normal range (or relative to a baseline) may trigger one or more operations, such as therapy parameter re-optimization discussed above, and may further involve increased monitoring or diagnostic operations, therapy delivery, patient or physician alerting, communication of warning and/or device/ physiological data to an external system (e.g., advanced patient management system) or other responsive operation.

An ECG signal 305 is plotted in FIG. 6B as a signal amplitude 350 on the ordinate versus time on the abscissa. One cardiac cycle is illustrated. The P portion of the ECG signal 305 may be defined using a P-window 335 that opens at a time 336 and closes at a time 337. A source separation performed on the ECG signal 305 within the P-window 335 produces the P vector 310 illustrated on a polar plot 330. The angle of the P vector 310 indicates the angle of the vector summation of the depolarization wavefront during the time of the P-window 335 for the ECG signal 305.

The ST portion of the ECG signal 305 may be defined using an ST-window 345 that opens at a time 346 and closes at a time 347. A source separation or other appropriate operation performed on the ECG signal 305 within the ST-window 345 produces the ST vector 350 illustrated on a polar plot 340. The angle of the ST vector 350 indicates the angle of the vector summation of the depolarization wavefront during the time of the ST-window 345 for the ECG signal 305. The P vector 310, ST vector 350 or other cardiac signal vector may be acquired as baselines, for future comparisons. As discussed above, detection of a cardiac signal vector characteristic beyond a predetermined baseline or threshold may trigger one or more responsive operations, such as re-optimization of intrinsic and therapy-based cardiac activation sequence characteristics and therapy parameters.

Figure 7:
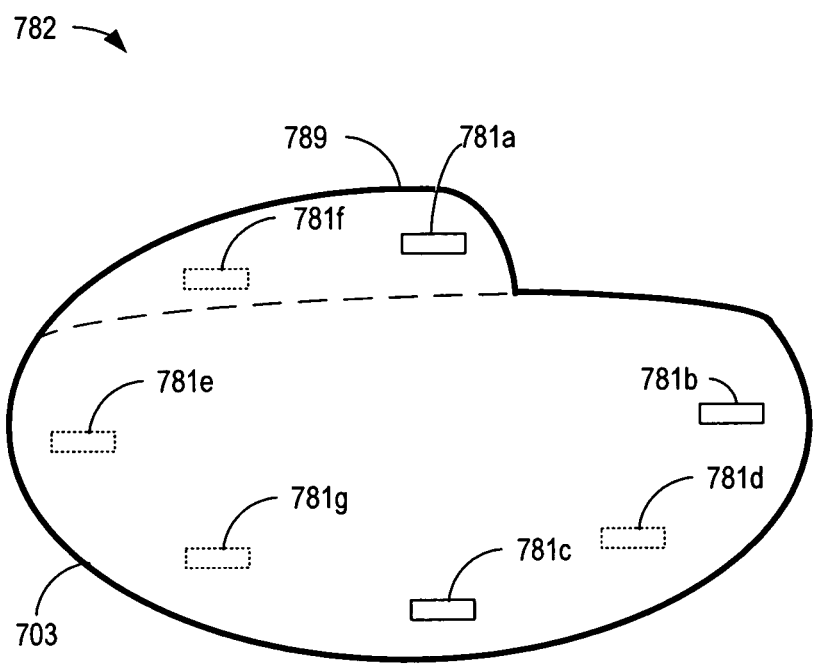
FIG. 7 is a side view of an implantable cardiac device in accordance with the present invention, having at least three electrodes.

FIG. 7 is a top view of an implantable therapy delivery device 782 in accordance with an embodiment of the present invention, having at least three electrodes. Although multiple electrodes are illustrated in FIG. 7 as located on the can, typically the can includes one electrode, and other electrodes are coupled to the can using a lead. The therapy delivery device 782 shown in the embodiment illustrated in FIG. 7 includes a first electrode 781a, a second electrode 781b, and a third electrode 781c provided with a can 703. The therapy delivery device 782 is configured to detect and record cardiac activity. The therapy delivery device 782 is also configured to delivery a cardiac electrical therapy, such as cardiac resynchronization therapy.

The can 703 is illustrated as incorporating a header 789 that may be configured to facilitate removable attachment between one or more leads and the can 703. The can 703 may include any number of electrodes positioned anywhere in or on the can 703, such as optional electrodes 781d, 781e, 781f, and 781g. Each electrode pair provides one vector available for the sensing of ECG signals, and may also be configured for therapeutic energy delivery.

Figure 8:
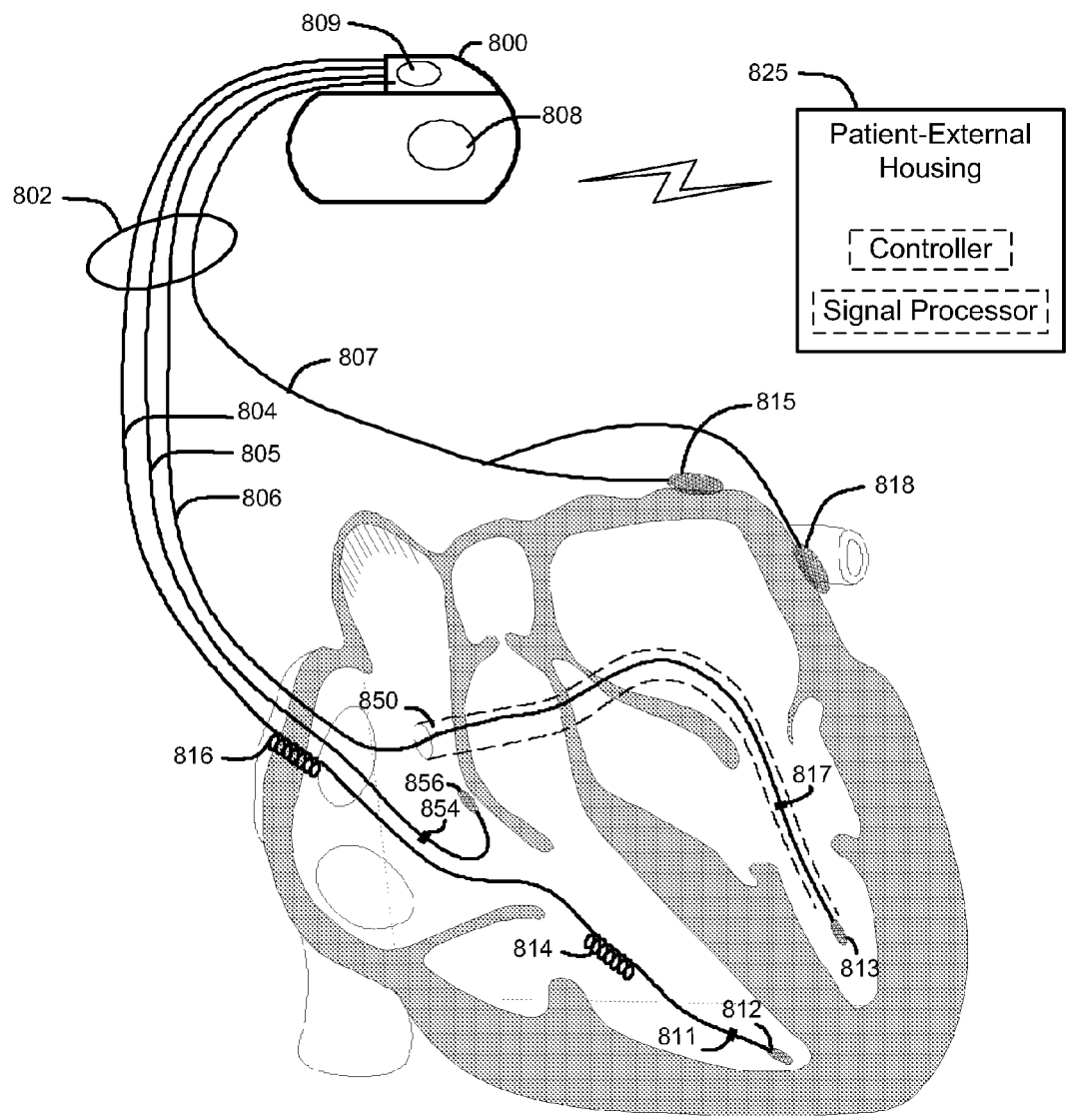
FIG. 8 is a diagram of an implantable cardiac device with leads implanted within a patient's heart, the implantable cardiac device configured to implement algorithms in accordance with embodiments of the present invention.

Referring now to FIG. 8, there is shown a cardiac rhythm management (CRM) system that may be used to implement a cardiac therapy and optimization methodology in accordance with the present invention. The CRM system in FIG. 8 includes a pacemaker/defibrillator 800 enclosed within a housing and coupled to a lead system 802. The housing and/or header of the pacemaker/defibrillator 800 may incorporate one or more can or indifferent electrodes 808, 809 used to provide electrical stimulation energy to the heart and/or to sense cardiac electrical activity. The pacemaker/defibrillator 800 may utilize all or a portion of the device housing as a can electrode 808. The pacemaker/defibrillator 800 may include an indifferent electrode 809 positioned, for example, on the header or the housing of the pacemaker/defibrillator 800. If the pacemaker/defibrillator 800 includes both a can electrode 808 and an indifferent electrode 809, the electrodes 808, 809 typically are electrically isolated from each other.

The lead system 802 is used to detect cardiac electrical signals produced by the heart and to provide electrical energy to the heart under certain predetermined conditions to treat cardiac arrhythmias. The lead system 802 may include one or more electrodes used for pacing, sensing, and/or defibrillation. In the embodiment shown in FIG. 8, the lead system 602 includes an intracardiac right ventricular (RV) lead system 804, an intracardiac right atrial (RA) lead system 805, and an intracardiac left ventricular (LV) lead system 806. An extracardiac left atrial (LA) lead system 807 is employed.

The CRM system illustrated in FIG. 8 is configured for biventricular or biatrial pacing. The lead system 802 of FIG. 8 illustrates one embodiment that may be used in connection with the cardiac therapy and optimization processes described herein. Other leads and/or electrodes may additionally or alternatively be used. For example, the CRM system may pace multiple sites in one cardiac chamber via multiple electrodes within the chamber. This type of multisite pacing may be employed in one or more of the right atrium, left atrium, right ventricle or left ventricle. Multisite pacing in a chamber may be used for example, to increase the power and or synchrony of cardiac contractions of the paced chamber.

The lead system 802 may include intracardiac leads 804, 805, 806 implanted in a human body with portions of the intracardiac leads 804, 805, 806 inserted into a heart. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 8, the lead system 802 may include one or more extracardiac leads 807 having electrodes 815, 818, e.g., epicardial electrodes, positioned at locations outside the heart for sensing and pacing one or more heart chambers. In some configurations, the epicardial electrodes may be placed on or about the outside of the heart and/or embedded in the myocardium from locations outside the heart.

The right ventricular lead system 804 illustrated in FIG. 8 includes an SVC-coil 816, an RV-coil 814, an RV-ring electrode 811, and an RV-tip electrode 812. The right ventricular lead system 804 extends through the right atrium and into the right ventricle.

In particular, the RV-tip electrode 812, RV-ring electrode 811, and RV-coil electrode 814 are positioned at appropriate locations within the right ventricle for sensing and delivering electrical stimulation pulses to the heart. The SVC-coil 816 is positioned at an appropriate location within the right atrium chamber of the heart or a major vein leading to the right atrial chamber.

In one configuration, the RV-tip electrode 812 referenced to the can electrode 808 may be used to implement unipolar pacing and/or sensing in the right ventricle. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 813 and an LV proximal electrode 817 located at appropriate locations in or about the left ventricle for pacing and/or sensing the left ventricle. The left ventricular lead 806 may be guided into the right atrium of the heart via the superior vena cava. From the right atrium, the left ventricular lead 806 may be deployed into the coronary sinus ostium, the opening of the coronary sinus 850. The lead 806 may be guided through the coronary sinus 850 to a coronary vein of the left ventricle. This vein is used as an access pathway for leads to reach the surfaces of the left ventricle which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 808. The LV distal electrode 813 and the LV proximal electrode 817 may be used together as bipolar sense and/or pace electrodes for the left ventricle. The lead system 802 in conjunction with the pacemaker/defibrillator 800 may provide bradycardia pacing therapy to maintain a hemodynamically sufficient heart rate. The left ventricular lead 806 and the right ventricular lead 804 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from heart failure.

The right atrial lead 805 includes a RA-tip electrode 856 and an RA-ring electrode 854 positioned at appropriate locations in the right atrium for sensing and pacing the right atrium. In one configuration, the RA-tip 856 referenced to the can electrode 808, for example, may be used to provide unipolar pacing and/or sensing in the right atrium. In another configuration, the RA-tip electrode 856 and the RA-ring electrode 854 may be used to effect bipolar pacing and/or sensing.

Figure 9:
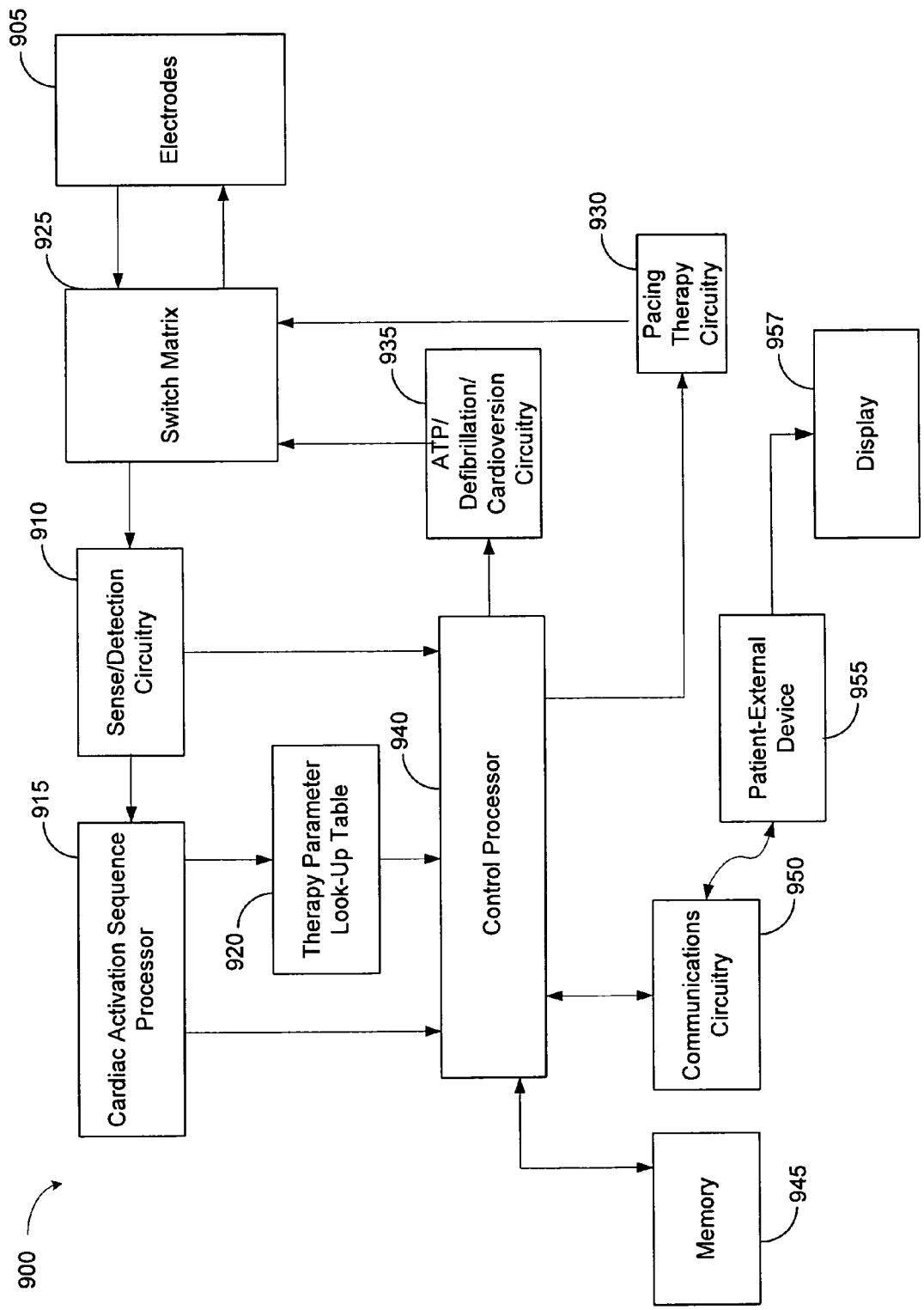
FIG. 9 is a block diagram of various components of a cardiac device (implantable, patient-external or a combination of both) that implements algorithms in accordance with embodiments of the present invention.

Referring now to FIG. 9, there is shown a block diagram of an embodiment of a therapy delivery system 900 suitable for implementing cardiac therapy and optimization methodologies of the present invention. Therapy delivery system 900 may be incorporated in a patient-implantable therapy device, such as those described above, or in a patient-external therapy device or system, such as is shown in FIG. 8 with reference to control and signal processing components disposed in a patient-external housing 825. Therapy delivery system 900 may also be configured such that one or more components or functions are distributed between implantable and patient-external therapy devices. For example, one or more of control, signal processing, sensing, and energy delivery may be implemented using both implantable and patient-external devices and/or processes.

FIG. 9 shows a therapy delivery system 900 divided into functional blocks. It is understood by those skilled in the art that there exist many possible configurations in which these functional blocks can be arranged. The example depicted in FIG. 9 is one possible functional arrangement. Other arrangements are also possible. For example, more, fewer or different functional blocks may be used to describe a cardiac system suitable for implementing cardiac therapy and optimization processes of the present invention. In addition, although the therapy delivery system 900 depicted in FIG. 9 contemplates the use of a programmable microprocessor-based logic circuit, other circuit implementations may be utilized.

The therapy delivery system 900 includes a control processor 940 capable of controlling the delivery of pacing pulses or, if so configured, defibrillation shocks to the right ventricle, left ventricle, right atrium and/or left atrium. The pacing therapy circuitry 930 may be configured to generate pacing pulses for treating bradyarrhythmia, for example, or for synchronizing the contractions of contralateral heart chambers using biatrial and/or biventricular pacing.

The therapy delivery system 900 includes a cardiac activation sequence processor 915 coupled to sense/detection circuitry 910. The cardiac activation sequence processor 915 is configured to produce a cardiac signal vector of a type described hereinabove. The control processor 940 is preferably configured to perform the baseline generation and comparison operations discussed above for intrinsic and therapy-based cardiac activation sequence characteristics, and to optimize therapy parameters as previously discussed. The control processor 940 also interacts with a therapy parameter look-up table 920 in a manner previously described.

The therapy delivery system 900 may also include arrhythmia discrimination circuitry (not shown) configured to classify cardiac rhythms, such as by use of rate-based and/or morphological-based algorithms operating on detected cardiac signals. The arrhythmia discrimination circuitry typically operates to detect atrial and/or ventricular tachyarrhythmia or fibrillation using a multiplicity of discrimination algorithms. Under control of the control processor 940, the pacing/cardioversion/defibrillation circuitry 935 is capable of generating high energy shocks to terminate the tachyarrhythmia episodes (e.g., antitachycardia pacing (ATP), cardioversion, and defibrillation therapies), as determined by the arrhythmia discriminator circuitry.

Pacing therapy circuitry 930 is configured to control pacing pulse generation in accordance with a variety of pacing modes and therapies, including resynchronization therapies. Pacing therapy circuitry 930 is also configured to generate pacing pulses to implement cardiac therapy and optimization processes described hereinabove.

The pacing pulses and/or defibrillation shocks are delivered via multiple cardiac electrodes 905 electrically coupled to a heart and disposed at multiple locations on the skin or within, on, or about the heart. One or more electrodes 905 may be disposed over, in, on, or about each heart chamber or at multiple sites of one heart chamber. The electrodes 905 are coupled to switch matrix 925 circuitry that is used to selectively couple the electrodes 905 to the sense circuitry 910 and the therapy circuitry 930, 935.

The therapy delivery system 900 is typically powered by an electrochemical battery (not shown). A memory 945 stores data (electrograms from multiple channels, timing data, etc.) and program commands used to implement the cardiac pacing therapies, rhythm discrimination if applicable, and therapy optimization processes described herein along with other features. Data and program commands may be transferred between the therapy delivery system 900 and a patient-external device 955 via telemetry-based communications circuitry 950.

The patient-external device 955 may be implemented as a programmer, an APM system or other external computational resource. A display 957 of a user interface of the patient-external device 955 is typically provided to facilitate user interaction with the patient-external device 955 and the cardiac therapy device. Data transferred from the cardiac therapy device to the patient-external device 955 may be organized in a manner useful for presentation to a clinician.

A user interface may be coupled to the APM system allowing a physician to remotely monitor cardiac functions, as well as other patient conditions, and to interact with a cardiac therapy device in a manner discussed above. The user interface may be used by the clinician to access information available via the APM system. The clinician may also enter information via the user interface for setting up the pacing output configuration functionality and optimizing pacing therapies. For example, the clinician may select particular sensors, hemodynamic status indicators, indicator levels or sensitivities, and/or electromechanical parameters. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in an implantable or patient-external cardiac therapy device, such as a pacemaker or pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:
   a plurality of electrodes configured for at least sensing cardiac electrical activity and energy delivery;
   a signal processor coupled to the electrodes and configured to produce a cardiac signal vector on a polar plot that originates at an atrioventricular (AV) node of a subject's heart, the cardiac signal vector associated with all or a portion of one or more cardiac activation sequences; and
   a controller coupled to the electrodes and the signal processor, the controller configured to:
   adjust a pacing parameter to elicit a cardiac signal vector indicative of one of pacing-dominant cardiac activation and intrinsic-dominant cardiac activation,
   continue to adjust the pacing parameter to elicit a cardiac signal vector indicative of the other of the pacing-dominant cardiac activation and the intrinsic-dominant cardiac activation,
   detect a change in an axis angle or a magnitude of the cardiac signal vector in response to the adjustment of the pacing parameter,
   define the change in the axis angle or the magnitude of the cardiac signal vector as a transition between the pacing-dominant cardiac activation and intrinsic-dominant cardiac activation; and
   store the adjusted pacing parameters to define a transition region.

2. The system of claim 1, wherein the controller is configured to iteratively adjust the pacing parameter until a pacing parameter setting that produces a cardiac fusion response is identified.

3. The system of claim 1, wherein the controller is disposed within an implantable housing, a patient-external housing, or distributed in both the implantable and patient-external housing.

4. The system of claim 1, wherein the signal processor is disposed within an implantable housing, a patient-external housing, or distributed in both the implantable and patient-external housing.

5. The system of claim 1, wherein the plurality of electrodes comprise implantable electrodes, cutaneous electrodes, or a combination of implantable and cutaneous electrodes.

6. The system of claim 1, further comprising an implantable housing, wherein the controller and the signal processor are provided in the housing, and the electrodes comprise implantable electrodes coupled to, or provided on, the housing.

7. The system of claim 1, further comprising a patient-external housing, wherein the controller and the signal processor are provided in the housing, and the electrodes comprise cutaneous electrodes coupled to the housing.

8. The system of claim 1, wherein the pacing parameter comprises A-V delay.

9. The system of claim 1, wherein the controller is coupled to memory, the memory configured to store a look-up table comprising pacing parameters associated with one or both of heart rate and patient condition, the pacing parameters established to produce a cardiac fusion pacing response.

10. The system of claim 9, wherein the controller is configured to update the look-up table with updated pacing parameters in response to identification of a change in the cardiac signal vector characteristic being indicative of pacing-dominant cardiac activation or intrinsic-dominant cardiac activation, the updated pacing parameters established to produce the cardiac fusion pacing response for the patient.

11. The system of claim 9, wherein the controller, in response to identification of a change in the cardiac signal vector being indicative of a change in intrinsic-dominant cardiac activation, is configured to update the look-up table with updated baselines characterizing each of the patient's intrinsic-dominant cardiac activation and pacing-dominant cardiac activation responses.

12. A system, comprising:
   a plurality of electrodes configured for at least sensing cardiac electrical activity and energy delivery;
   a signal processor coupled to the electrodes and configured to produce a cardiac signal vector on a polar plot that originates at an atrioventricular (AV) node of a subject's heart, the cardiac signal vector associated with all or a portion of one or more cardiac activation sequences; and
   a controller coupled to memory, the electrodes, and the signal processor, the controller configured to:
   adjust a pacing parameter to elicit a cardiac signal vector indicative of one of pacing-dominant cardiac activation and intrinsic-dominant cardiac activation,
   continue to adjust the pacing parameter settings to elicit a cardiac signal vector indicative of the other of the pacing-dominant cardiac activation and the intrinsic-dominant cardiac activation pacing responses,
   detect a change in an axis angle or a magnitude of the cardiac signal vector in response to the adjustment of the pacing parameter;
   define a change above a predetermined threshold value in the axis angle or the magnitude of the cardiac signal vector as a transition between the pacing-dominant cardiac activation and the intrinsic-dominant cardiac activation, store at least one adjusted pacing parameter setting in the memory to record the transition between the pacing-dominant cardiac activation and the intrinsic-dominant cardiac activation responses, and deliver a pacing therapy that uses the stored pacing parameter setting.

13. The system of claim 12, wherein the controller is disposed within an implantable housing, a patient-external housing, or distributed in both the implantable and patient-external housing.

14. The system of claim 12, wherein the signal processor is disposed within an implantable housing, a patient-external housing, or distributed in both the implantable and patient-external housing.

15. The system of claim 12, wherein the plurality of electrodes comprise implantable electrodes, cutaneous electrodes, or a combination of implantable and cutaneous electrodes.

16. The system of claim 12, further comprising an implantable housing, wherein the controller and the signal processor are provided in the housing, and the electrodes comprise implantable electrodes coupled to, or provided on, the housing.

17. The system of claim 12, further comprising a patient-external housing, wherein the controller and the signal processor are provided in the housing, and the electrodes comprise cutaneous electrodes coupled to the housing.

18. The system of claim 12, wherein the controller is configured to iteratively adjust the pacing parameter until the pacing parameter setting that produces a cardiac fusion response is identified.

19. The system of claim 12, wherein the controller is configured to store a look-up table in the memory, the look-up table comprising pacing parameters associated with one or both of heart rate and patient condition, the pacing parameters comprising the pacing parameter setting established to produce a cardiac fusion response.

20. The system of claim 19, wherein the controller is configured to update the look-up table with updated pacing parameters in response to a change in the cardiac signal vector characteristic indicative of pacing-dominant cardiac activation or intrinsic-dominant cardiac activation, the updated pacing parameters comprising the pacing parameter setting established to produce the cardiac fusion response.

21. The system of claim 19, wherein the controller, in response to a change in the cardiac signal vector characteristic indicative of a change in intrinsic-dominated cardiac activation, is configured to update the look-up table with updated baselines characterizing each of the patient's intrinsic-dominated cardiac activation and pacing-dominant cardiac activation responses.

* * * * *